(12) United States Patent
Safavy (10) Patent No.: US 6,191,290 B1
(45) Date of Patent: Feb. 20, 2001

(54) TAXANE DERIVATIVES FOR TARGETED THERAPY OF CANCER

(75) Inventor: Ahmad Safavy, Birmingham, AL (US)

(73) Assignee: UAB Research Foundation, Birmingham, AL (US)

( * ) Notice: Under 35 U.S.C. 154(b), the term of this patent shall be extended for 0 days.

(21) Appl. No.: 09/510,896

(22) Filed: Feb. 23, 2000

Related U.S. Application Data (60) Provisional application No. 60/121,642, filed on Feb. 24, 1999, now abandoned.

(51) Int. Cl.⁷ ....................... C07D 305/14; A61K 31/337
(52) U.S. Cl. ........................... 549/510; 549/511; 514/449
(58) Field of Search ............................ 514/449; 549/510, 549/511

(56) References Cited

U.S. PATENT DOCUMENTS

| | | | | |
|---|---|---|---|---|
| 4,960,790 | * | 10/1990 | Stella et al. ........................... | 514/449 |
| 5,580,899 | * | 12/1996 | Mayhew et al. ...................... | 514/449 |
| 5,643,575 | * | 7/1997 | Martinez et al. ................. | 424/194.1 |
| 5,939,567 | * | 8/1999 | Mayhew et al. ...................... | 549/510 |

* cited by examiner

*Primary Examiner*—Ba K. Trinh
(74) *Attorney, Agent, or Firm*—Benjamin Aaron Adler (57) ABSTRACT

The present invention describes for the first time the design and synthesis of a soluble tumor-directed paclitaxel prodrug which may establish a new mode of utilization of the taxane class of anticancer agents in cancer therapy.

14 Claims, 8 Drawing Sheets

1: Pacltiaxel: R = Bz, R′ = Ac
2: Docetaxel: R = *tert*-BuO, R′ = H
3: Paclitaxel - 2′ - succinate: R″ = -CO(CH$_2$)$_2$-CO$_2$H
4: Paclitaxel - 2′ - glutarate: R″ = -CO(CH$_2$)$_3$-CO$_2$H

TAXANE DERIVATIVES FOR TARGETED THERAPY OF CANCER

CROSS-REFERENCE TO RELATED APPLICATIONS

This application claims benefit of priority of provisional U.S. Serial No. 60/121,642, filed Feb. 24, 1999, now abandoned.

BACKGROUND OF THE INVENTION

1. Field of the Invention

The present invention relates generally to the biochemical pharmacology of the anti-cancer drug, paclitaxel. More specifically, the present invention relates to the design and synthesis of the first tumor-directed derivatives of paclitaxel.

2. Description of the Related Art

Figure 1:
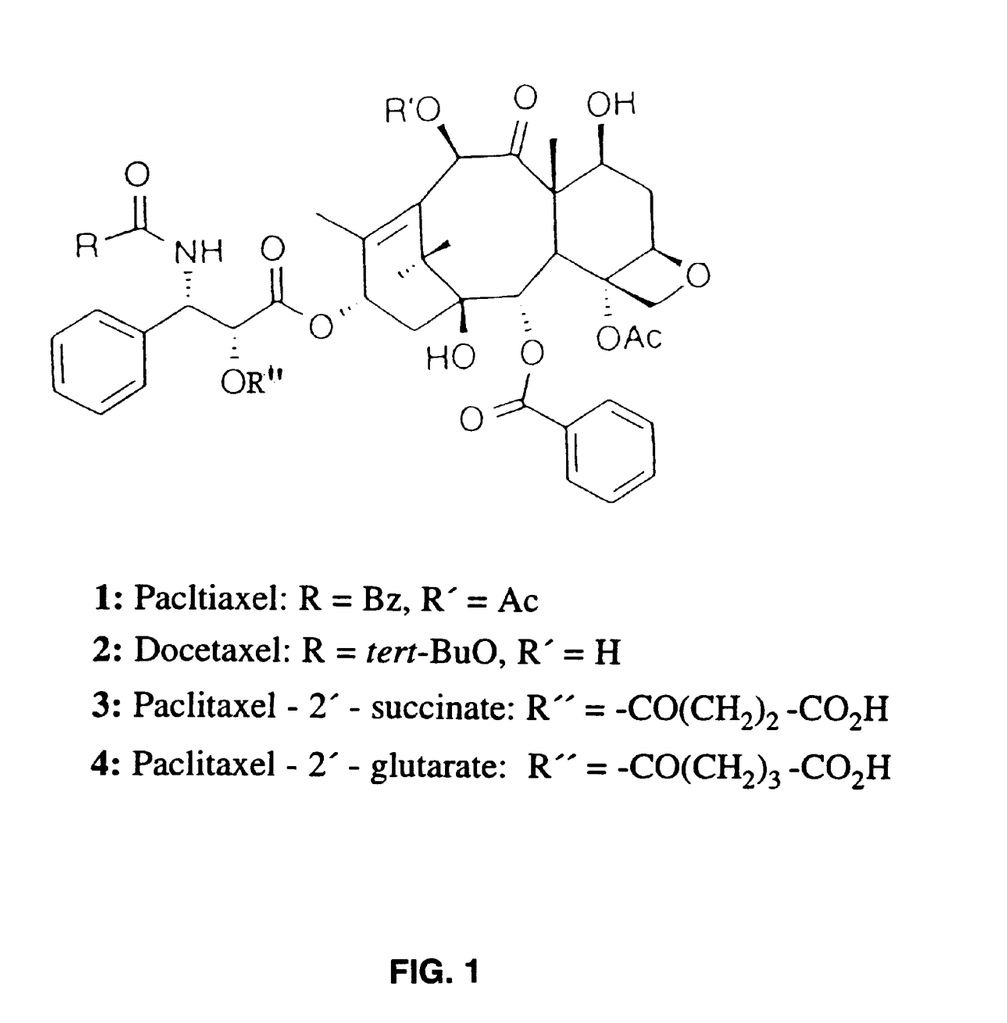
FIG. 1 shows structures of paclitaxel (Taxol, 1) and taxotere (Docetaxel, 2). Paclitaxel was derivatized in this study, with either succinic anhydride to 3 or with glutaric anhydride to 4, for conjugation to the PEGBBN [7–13] as shown in FIG. 2.

The diterpenoid molecule paclitaxel (taxol) (FIG. 1), extracted in 1971 from the western yew, *Taxus brevifolia* (1), and taxotere (docetaxel) (2) are considered to be two of the most important and promising anticancer drugs currently in clinical use for breast and ovarian cancers which also hold promise for the treatment of skin, lung and head and neck carcinomas (3, 4). Paclitaxel was approved by the FDA earlier this decade for the treatment of advanced ovarian cancer and breast cancer after showing outstanding efficacies in the chemotherapy of malignancies particularly in refractory ovarian and breast cancers. Docetaxel, a semi-synthetic derivative of paclitaxel, has also shown exceptional clinical results and was approved by the FDA for the treatment of breast cancer in 1996 and is now in phase II and III clinical trials for lung cancer and ovarian cancer (3, 4).

Perhaps one of the most distinguishing properties of paclitaxel is its high activity against solid tumors compared to leukemias, when tested in animal models. The drug has also been reported to be a radiosensitizer. At the molecular level, paclitaxel exerts its antitumor activity through the stabilization of microtubule assemblies thus interrupting mitosis and the cell division process. The taxol-induced microtubules have been shown to be resistant to depolymerization. Based on this mechanism and the fact that taxol increases the fraction of cells in $G_2$ or M phase, Tishler et al. (5), and more recently, O'Donnell et al. (6), reported a radiosensitizing effect for taxol on G18 human astrocytoma cells and in nude mice bearing Burkitts lymphoma xenografts, respectively. Furthermore, Distefano et al. have shown apoptosis-inducing properties for Taxol (7). These observations may result in still more applications for taxanes in the form of combined modality therapy.

Despite these ideal therapeutic features, paclitaxel suffers from such significant drawbacks as aqueous insolubility and side-effects at the clinically administered doses. The present formulation of this drug contains 30 mg of Taxol in 5 mL of a 50/50 mixture of Cremophore EL (polyhydroxylated castor oil, a solubilizing surfactant) and ethanol. Cremophore EL has been reported to cause histamine release and result in severe allergic reactions and cause potential clinical problems (8, 9). Reported side effects of the drug, based on clinical trials, include neutropenia, mucositis, cardiac and neurological toxicities in addition to hypersensitivity (10–14).

Taxol is nearly slightly insoluble in water (around 0.25 µg/mL) and this has created significant problems in developing suitable pharmaceutical formulations useful for chemotherapy. Some formulations of taxol for injection or I.V. infusion have been developed utilizing CREMOPHOR EL.RTM (polyoxyethylated castor oil) as the drug carrier because of taxol's aqueous insolubility. For example, taxol supplied by the NCI has been formulated in 50% CREMOPHOR EL.RTM. and 50% dehydrated alcohol. CREMOPHOR EL.RTM., however, is itself toxic and produces, when given in a large volume single dose without taxol, vasodilation, labored breathing, lethargy, hypotension and death in dogs. Therefore, the use of this carrier would not be recommended.

In an attempt to increase taxol's solubility and to develop more safe clinical formulations, studies have been directed to synthesizing taxol analogs where 2'- and/or 7-position is derivatized with groups that would enhance water solubility. These efforts yielded protaxol compounds that are more water soluble than the parent compound and that deploy the cytotoxic properties upon activation.

It would be highly desirable, therefore, to develop a mechanism through which a soluble Taxol derivative could be delivered specifically to the site of the disease in a targeted fashion. Possible advantages of such an approach may include i) elimination of allergenic surfactants from the formulation due to increased solubility, ii) efficient delivery of the drug to micrometastatic hidden tumors, and iii) reduction of the administered dose as a result of site-specific delivery of the drug. The latter advantage should, in turn, lead to a reduction of toxicity, enhancement in efficacy, lower drug doses, and thereby safer, and more economic formulations.

Pretargeted therapy of malignancies has gained momentum during the past several years based on its well-justified rationale, the efficient delivery of the oncolytic agent to the neoplastic tissue. Receptor-based targeted treatment of cancer through the application of tumor-recognizing molecules has advanced considerably during the past several years with t h e development of monoclonal antibodies (15, 16), and later, the application of small molecule peptides capable of binding to tumor cell surface receptors (17). A number of drug, toxin, and radioisotope conjugates of tumor-recognizing molecules have been developed with some in clinical use currently. None of the designs of the large number of synthetic taxane derivatives reported so far, however, contain an element of specific tumor recognition. Despite the large body of work in this field, there are no reports of tumor-recognizing molecules of paclitaxel or any derivative of this drug.

Thus, the prior art is deficient in methods through which a soluble Taxol derivative could be delivered specifically to the site of the disease in a targeted fashion. The present invention fulfills this long-standing need and desire in the art.

SUMMARY OF THE INVENTION

The present invention demonstrates for the first time the design and synthesis of a soluble tumor-directed paclitaxel prodrug which may establish a new mode of utilization of the taxane class of anticancer agents in cancer therapy.

In one embodiment of the present invention, there is provided a pharmaceutical compound comprising a taxane moiety conjugated to a receptor ligand peptide. The taxane moiety can be a taxane derivative. Representative examples are paclitaxel (taxol), taxotere (docetaxel), and their analogs. The receptor ligand can be peptides such as bombesin/gastrin-releasing peptide (BBN/GRP) receptor-recognizing peptide (BBN[7–13]), a somatostatin receptor recognizing peptide, an epidermal growth factor receptor recognizing peptide, a monoclonal antibody or a receptor recognizing carbohydrate.

In another embodiment of the present invention, the pharmaceutical compound is water soluble and tumor directed. Specifically, such compound can readily dissolve in water at the concentration of 250 mg/ml or higher, corresponding to at least 40 mg/ml of the unconjugated paclitaxel. This is a major improvement considering the 0.25 mg/ml solubility of Taxol.

In still another embodiment of the present invention, there is provided a method of synthesizing the pharmaceutical compound described herein, comprising the steps of: conjugating covalently said receptor ligand peptide to a solubilizing linker; and ligating the peptide-conjugated linkers to said taxane moiety. Preferably, the ligation can occur at the sites selected from a taxane moiety such as 2-, 7- and 10-hydroxyl group of the taxane moiety with solubilizing linker and receptor recognizing moiety. As a result, the synthesized pharmaceutical compound has improved cytotoxicities in a concentration-dependent manner by a factor of 1.5–3 compared to corresponding unconjugated taxane moiety at an equimolar concentration.

In still yet another embodiment of the present invention, there is provided a method of treating an individual having a cancer by administering the pharmaceutical compound of the present invention to the individual. Preferably, the cancer is selected from the group consisting of breast cancer, ovarian cancer, skin carcinoma, lung carcinoma, head carcinoma and neck carcinoma. The pharmaceutical compound may be administered at a lower concentration range than that of the unconjugated paclitaxel by the means of injection or intravenous infusion.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

The present invention demonstrates that the pharmacologic efficacy of the antitumor agent paclitaxel (taxol) may be enhanced through derivatization of the drug to a water soluble tumor-recognizing conjugate. This work reports the design and synthesis of the first tumor-directed derivative of paclitaxel. A 7-aminoacid synthetic peptide, BBN [7–13], which binds to the cell surface bombesin/gastrin releasing peptide (BBN/GRP) receptor was conjugated to the paclitaxel 2'-hydroxy function by a heterobifunctional poly (ethylene glycol) linker. The resulting conjugate, designated PTXPEGBBN[7–13], was soluble to the upper limit of tested concentrations (150 mg/mL) which may be well below the saturation limit.

The cell binding capability of the conjugate was tested in an $[^{125}I]$-Tyr$^3$-bombesin cell binding inhibition assay using the unconjugated BBN[7–13]. The conjugate completely retained the receptor binding properties of the attached tumor-targeting peptide as compared with those of the unconjugated BBN[7–13]. Also, compared to unconjugated paclitaxel, the cytotoxicity of PTXPEGBBN[7–13] against NCI-H1299 cell line showed improvement by a factor of 3 (at 50 nM) and 2.3 (at 25 nM). These results describe for the first time the design and synthesis of a soluble tumor-directed paclitaxel prodrug which may establish a new mode of utilization of this drug in cancer therapy.

The present invention is directed to a pharmaceutical compound comprising a taxane moiety conjugated to a receptor ligand peptide. The taxane moiety can be a taxane derivative. Representative examples are paclitaxel (taxol) and taxotere (docetaxel). The receptor ligand can be peptides such as bombesin/gastrin-releasing peptide (BBN/GRP) receptor-recognizing peptide (BBN[7–13]), a somatostatin receptor recognizing peptide, an epidermal growth factor receptor recognizing peptide, a monoclonal antibody or a receptor recognizing carbohydrate. Preferably, the pharmaceutical compound is water soluble and tumor directed. Specifically, such compounds of the present invention can readily dissolve in water at the concentration of 250 mg/ml or higher.

In still another embodiment of the present invention, there is provided a method of synthesizing the pharmaceutical compound disclosed herein, comprising the steps of: conjugating covalently said receptor ligand peptide to a solubilizing linker; and ligating the peptide-conjugated linkers to said taxane moiety. Preferably, the ligation can occur at a site selected from the group consisting of 2-, 7-, 10- or 2'-hydroxyl group of the taxane moiety, the solubilizing linker (for example PEG, a poly(aminoacid), a peptide, a protein or a carbohydrate and the receptor targeting peptide or antibody. As a result, the synthesized pharmaceutical compound has improved cytotoxicities in a concentration-dependent manner by a factor of 1.5–3 compared to corresponding unconjugated taxane moiety at an equimolar concentration.

In still yet another embodiment of the present invention, there is provided a method of treating an individual having a cancer by administering the claimed pharmaceutical compound to the individual. Preferably, the cancer is selected from the group consisting of breast cancer, ovarian cancer, skin carcinoma, lung carcinoma, head carcinoma and neck carcinoma. Still preferably, the pharmaceutical compound is administered at a lower concentration range than that of the free, unconjugated drug by the means of injection or intravenous infusion.

The following examples are given for the purpose of illustrating various embodiments of the invention and are not meant to limit the present invention in any fashion:

EXAMPE 1
Synthesis of Ternary Conjugate

A ternary conjugate (FIG. 2) was synthesized consisting of paclitaxel (PTX), poly(ethylene glycol) (PEG), and a bombesin-(BBN-)/gastrin-releasing peptide-(GRP-) receptor-recognizing peptide (BBN[7–13]) (18), as the first member of a series of soluble tumor-targeting paclitaxel derivatives. These novel molecules were designed based on the premises that the soluble conjugate will be guided by the receptor-specific peptide to home in on the tumor cell surface receptors, and that after internalization, the paclitaxel-PEG bond will be hydrolytically and/or enzymatically cleaved to release the cytotoxic cargo.

The high-priority step in the design of the paclitaxel conjugates of the present invention was the induction of water solubility into the molecule. Paclitaxl-polyethylene glycol conjugates have been reported recently by Greenwald et al. (19) and Li et al. (20). During the course of the present study, polyethylene glycol was independently identified as a potential "aqueous anchor" and the 2'-paclitaxel-polyethylene glycol system was considered as the soluble segment of the final conjugate. This selection was made after screening a number of candidates including several multimers of tetraethylene glycol with and without aminoacid pendants (21).

Interesting chemical and biological properties of polyethylene glycols have been extensively studied and some useful characteristics of this polymer have been noted. These include aqueous as well as organic solubilities, lack of immunogenicity, and favorable blood clearance patterns and in vivo behavior (22). Furthermore, in contrast to the reported paclitaxel-polyethylene glycol derivatives (19, 20), a heterobifunctional derivative of the polymer to be placed as a linker was used in this synthesis, bridging the peptide and the paclitaxel moieties.

Figure 2:
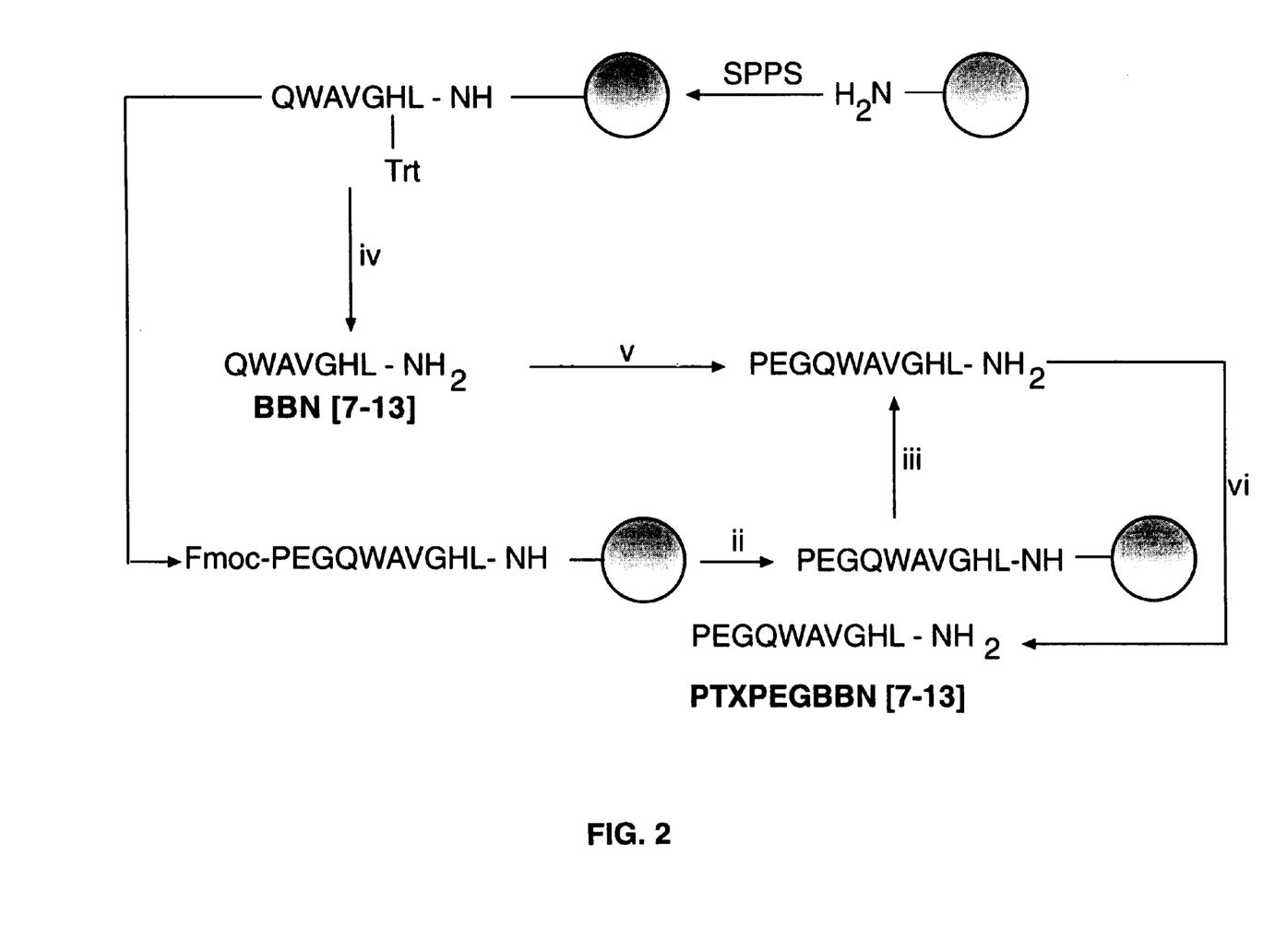
FIG. 2 shows the BBN/GRP receptor ligand peptide is made by solid-phase peptide synthesis (SPPS) through the Fmoc methodology on a Rink amide resin. Conjugation to the polyethylene glycol linker is carried out by both solid- (i–iii) and solution-phase (iv, v) techniques. Coupling to the paclitaxel nucleus was performed in solution (vi).

The construction of the molecule began with the solid-phase synthesis of the BBN[7–13] segment which, on completion, was ligated to the polyethylene glycol linker through both solid- and solution-phase techniques (FIG. 2).

Figure 3:
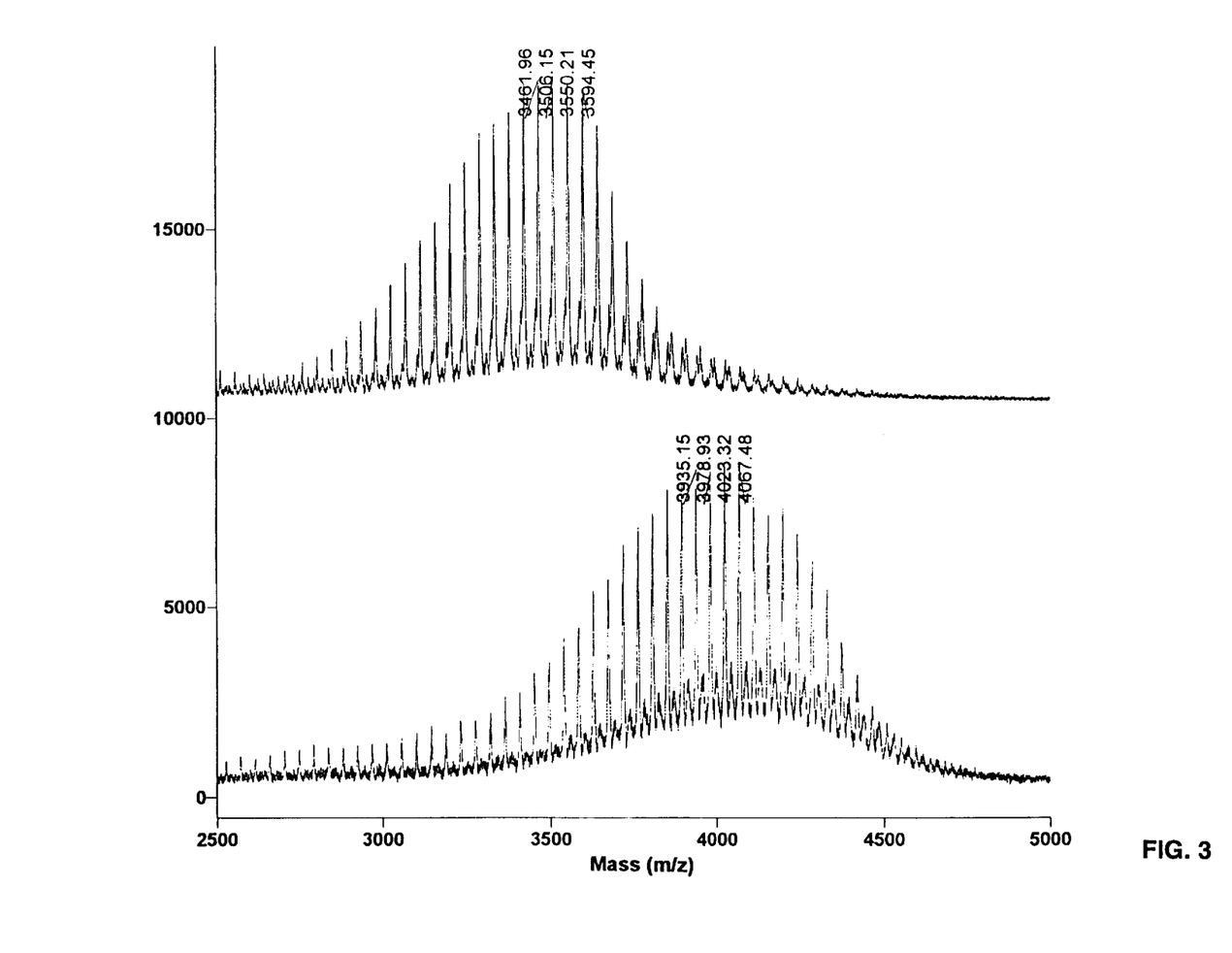
FIG. 3 shows the MALDI-TOF mass spectrum of the PEGBBN [7–13] conjugate as referenced to the unconjugated starting polyethylene glycol. The positive molecular weight shift shows formation of the expected product. Identical MS patterns and molecular weights were observed for both solid-phase and solution-phase products.
Figure 4A:
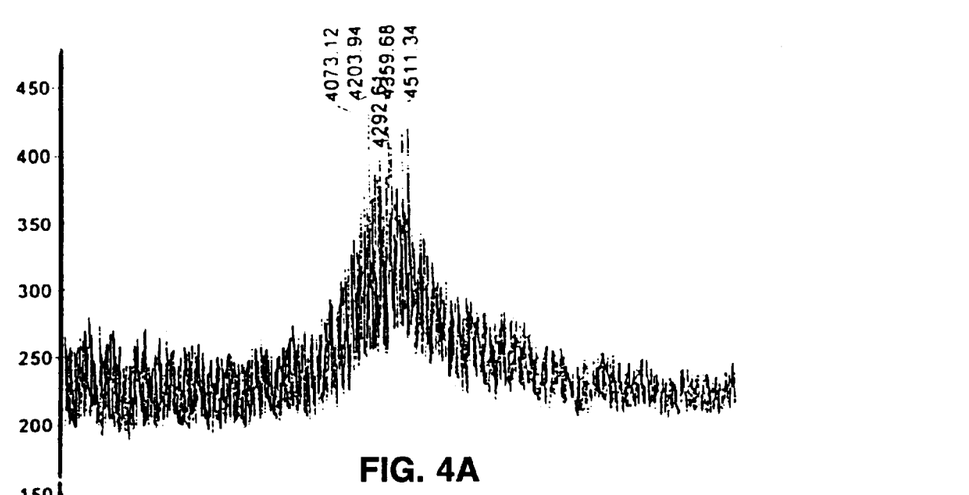
FIG. 4 shows the molecular weight growth as a measure of the reaction progress in the synthesis of the PIXPEGBBN [7–13]. Aliquouts of the reaction were withdrawn at certain time periods (A, 1 h; B, 5 h; C, 12 h; D, 19 h), and analyzed with MALDI-TOF mass spectrometry. The newly formed compound showed the calculated molecular weight.
Figure 4B:
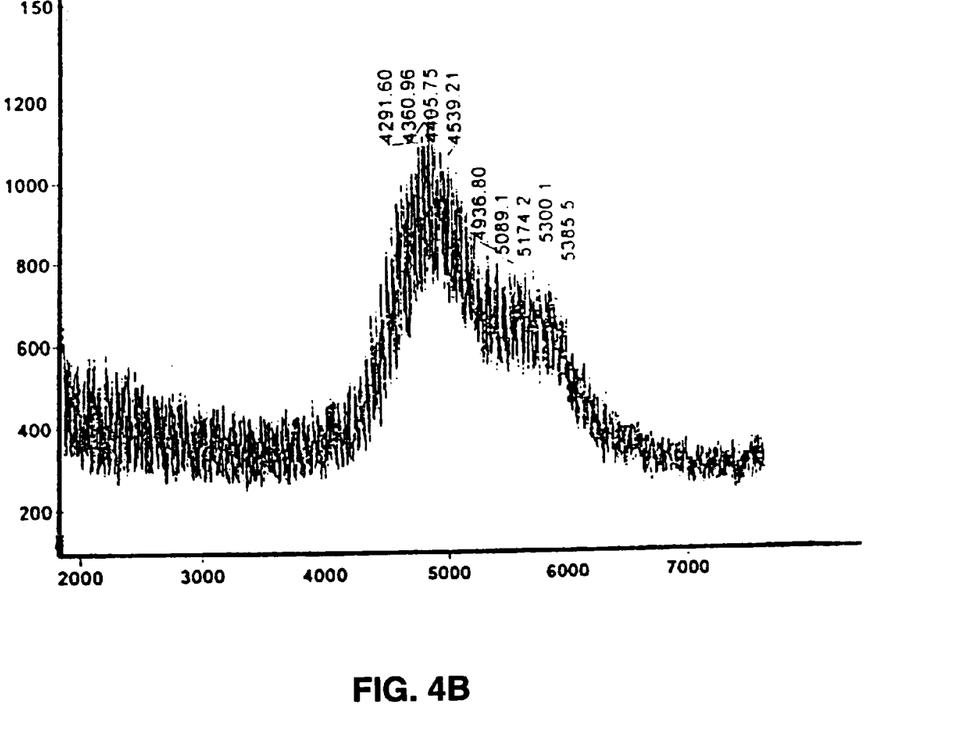
Figure 4C:
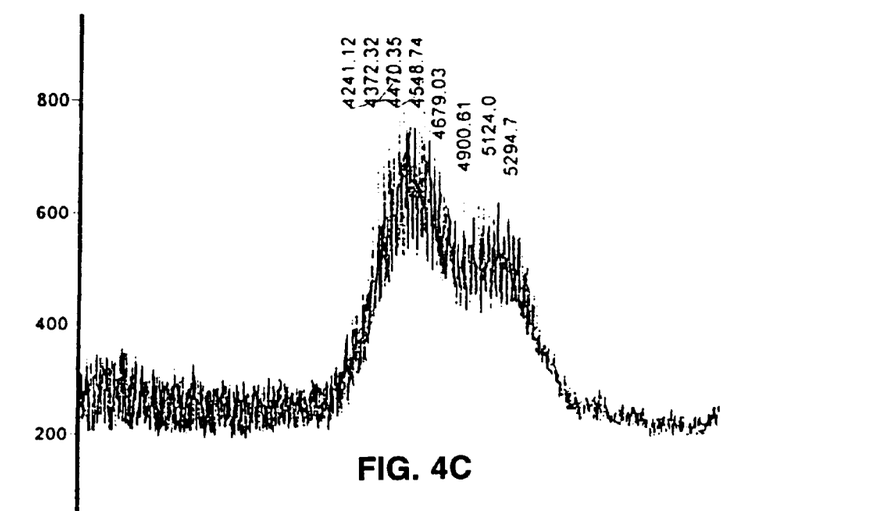
Figure 4D:
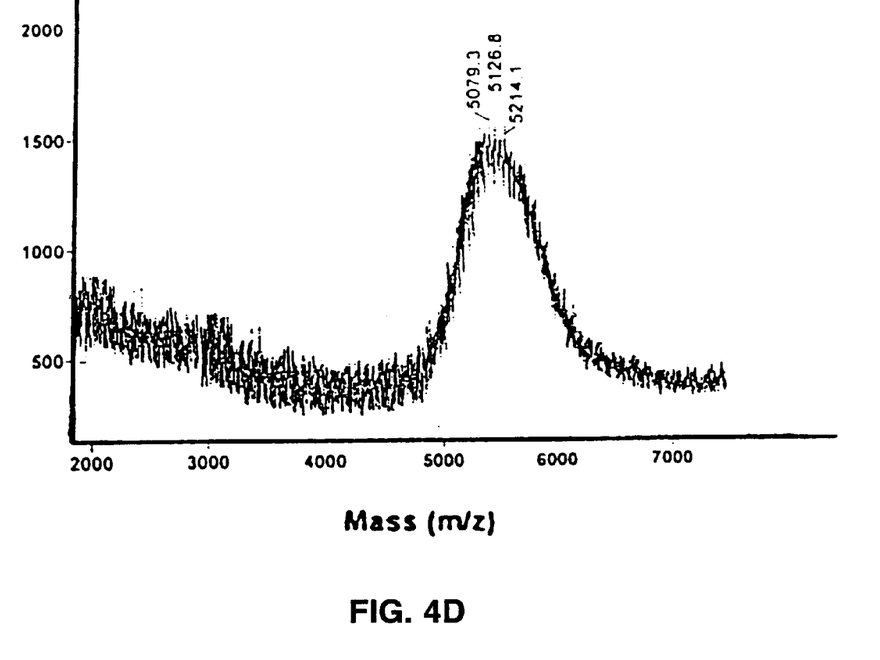

The homogeneity of the polyethylene glycol-BBN[7–13] conjugate was determined unambiguously by MALDI mass spectometry when a single group of peaks in the expected molecular weight range (mean 4000 Da) was observed (FIG. 3). Ligation of this conjugate to the paclitaxel pharmacophore was carried out in dichloromethane and in the presence of 2-ethoxy-1-ethoxycarbonyl-1,2-dihydroquinoline (EEDQ) or preferably with 0-(benzotriazol-1-yl)-1,1,3,3-tetramethyuronium hexamethyl phosphate (20). The homogeneous solution was stirred at 5° C. and the reaction progress was monitored by MALDI MS (FIG. 4). After 19 hours, the MALDI MS showed a newly formed product with a MW of 5200 Da in agreement with the calculated MW of the target product (FIG. 4D).

Prior to the biological evaluation of this compound, two key issues needed to be addressed: The overall water solubility and the cell surface receptor binding ability of the conjugate. The conjugate was readily soluble in aqueous solvents at up to 150 mg/mL solutions in water, 0.9% saline, 50 mM PBS (pH 7.4) and 50 mM acetate buffer (pH 4.0), resulting in free-flowing homogeneous solutions. Interestingly, the conjugate was also readily soluble in such organic solvents as methylene chloride, chloroform, methanol, ethanol, ethyl acetate, and dimethyl formamide (DMF). The unconjugated BBN [7–13] peptide was soluble only in DMF and alcohols, and as such, the PEG linker seems to play the role of a common universal solubilizer for both paclitaxel and peptide moieties.

EXAMPLE 2
Cell-Binding Efficiency

To evaluate the overall cell-binding efficiency of the conjugate, the ability of the Taxol conjugate to inhibit the binding of commercially supplied [$^{125}$I]-Tyr$^3$-BBN to BNR-11 cell line was compared with that of the free, unconjugated peptide. This cell line is derived from murine 3T3 fibroblasts and is stably transfected with GRPr (23) and has been used for receptor affinity evaluations of this peptide (18, 24). A human non-small cell lung carcinoma cell line (NCI-H1299) which has a significant but smaller number of BBN receptors (25) was also used.

The binding of the [$^{125}$I]-Tyr$^3$-BBN to BNR-11 and NCI-H1299 were 69%±1.6% and 19%±0.5%, respectively (TABLE 1). The binding inhibition studies showed that the conjugate inhibition of [$^{125}$I]-Tyr$^3$-BBN binding to both cell lines was around 80%, which was the same as that of the unconjugated BBN[7–13] peptide. The attachment of the 7-aminoacid sequence to a relatively large molecule, therefore, preserved entirely the receptor binding ability of the peptide and the presence of neither the polyethylene glycol spacer nor the paclitaxel nucleus, had any effect on the receptor binding ability of the peptide.

TABLE 1

[$^{125}$I]-Tyr$^3$-BBN binding and inhibition data for BBN[7-13] peptide and PTXPEGBBN[7-13] conjugate using BNR-11 and NCI-H1299 cell lines[a]

| Cell Line | % Binding [$^{125}$I]-Tyr$^3$-BBN | % Inhibition BBN[7-13] | % Inhibition PTXPEGBBN[7-13] |
|---|---|---|---|
| BNR-11 | 69 ± 1.6 | 80 ± 1.2 | 90 ± 0.3 |
| NCI-H1299 | 19 ± 0.5 | 81 ± 0.07 | 77 ± 0.6 |

[a]n = 3

EXAMPLE 3
Cytotoxic Effects Of The Paclitaxel Conjugate

To evaluate the cytotoxic effects of the paclitaxel conjugate, experiments were designed to compare these effects with the underivatized, unconjugated paclitaxel. The low-receptor density (RD) H1299 cells were used to demonstrate the extent of the sensitivity of a native, untransfected cell line to this form of treatment.

Figure 5:
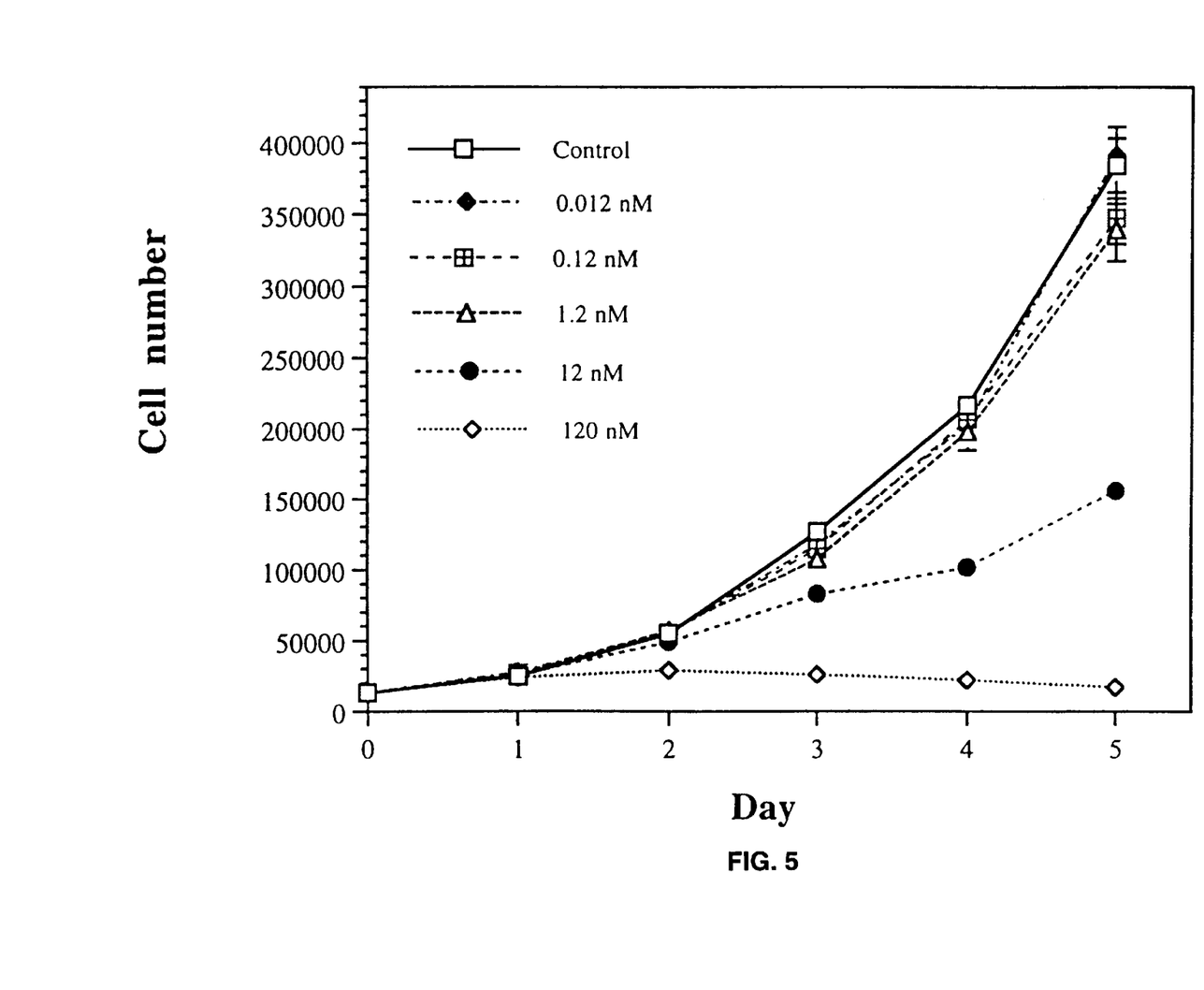
FIG. 5 shows growth inhibition curves for NCI-H1299 non-small cell lung carcinoma cell line after treatment with PIXPEGBBN [7–13] conjugate at days 1–5 at different concentrations of the conjugate: A 120 nM concentration of the conjugate results in total arrest of the cell growth. The growth inhibition is concentration-dependent sowing an $IC_{50}$ of 5 nM on day5.

Cells were exposed to the PTXPEGBBN[7–13] conjugate at different concentrations (0.012 nM–120 nM) and their growth was monitored daily against untreated control cells (FIG. 5). The upper limit of the concentration (120 nM) showed complete growth inhibition throughout the experiment duration (5 d) with the 10% of this concentration showing an inhibition of 60% on day 5. These results indicated 50% inhibitor concentrations ($IC_{50}$s) of 20 nM, 9 nM, and 6 nM at days 3, 4, and 5, respectively, and imply that the conjugation chemistry and the inclusion of the peptide in a larger molecule do not destroy its activity.

Figure 6:
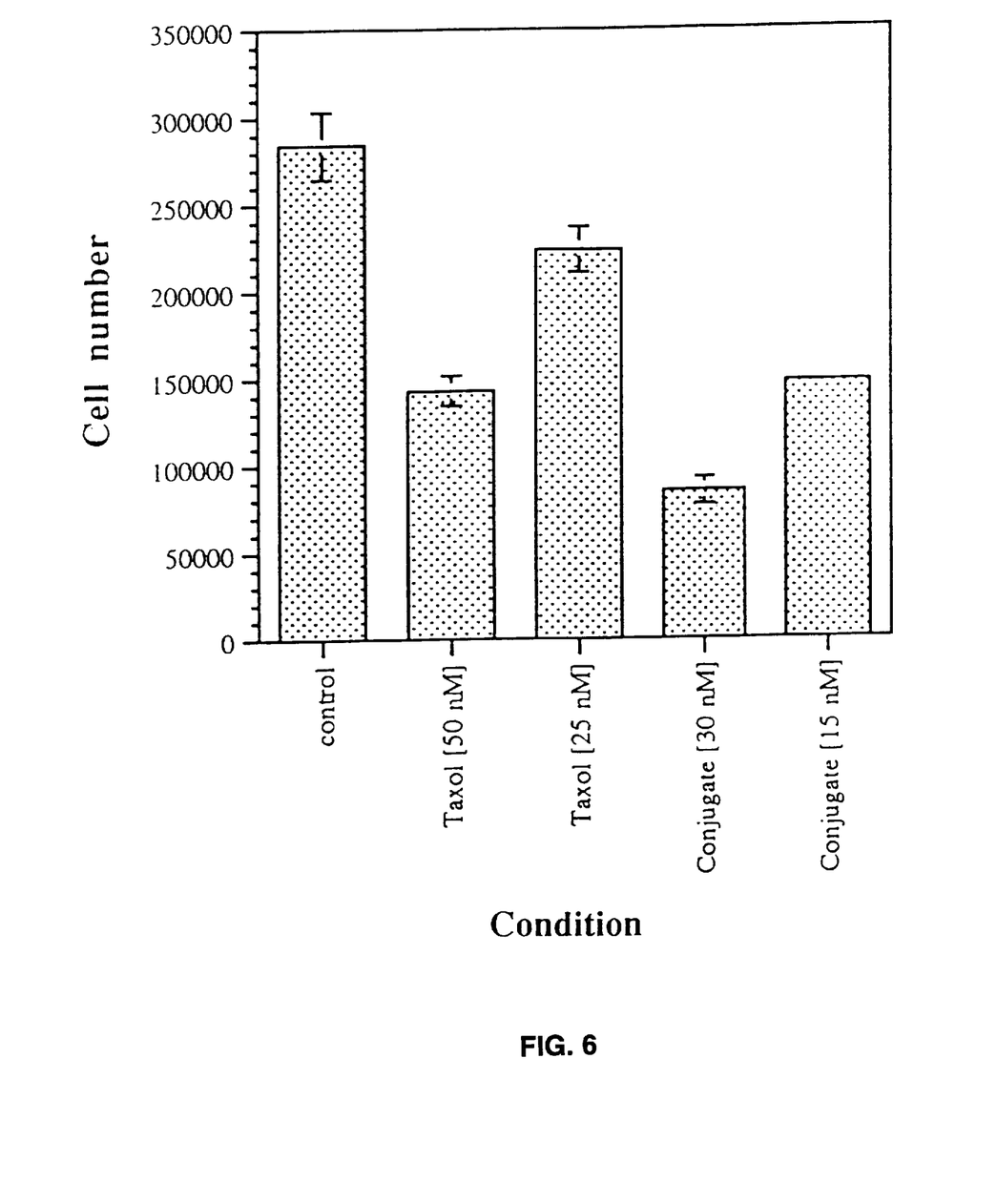
FIG. 6 shows cytotoxicity assays at day 4 post-treatment for the PTXPEGBBN[7–13] conjugate with underivatized paclitaxel as control. Cytotoxicity is evaluated at a conjugate:Taxol molar ratio of 60% and showing 53% (15 nM) and 70% (30 nM) cell destruction by the conjugate as compared to that for the unconjugated paclitaxel with 23%, and 51% at 25 nM and 50 nM, respectively.
Figure 7:
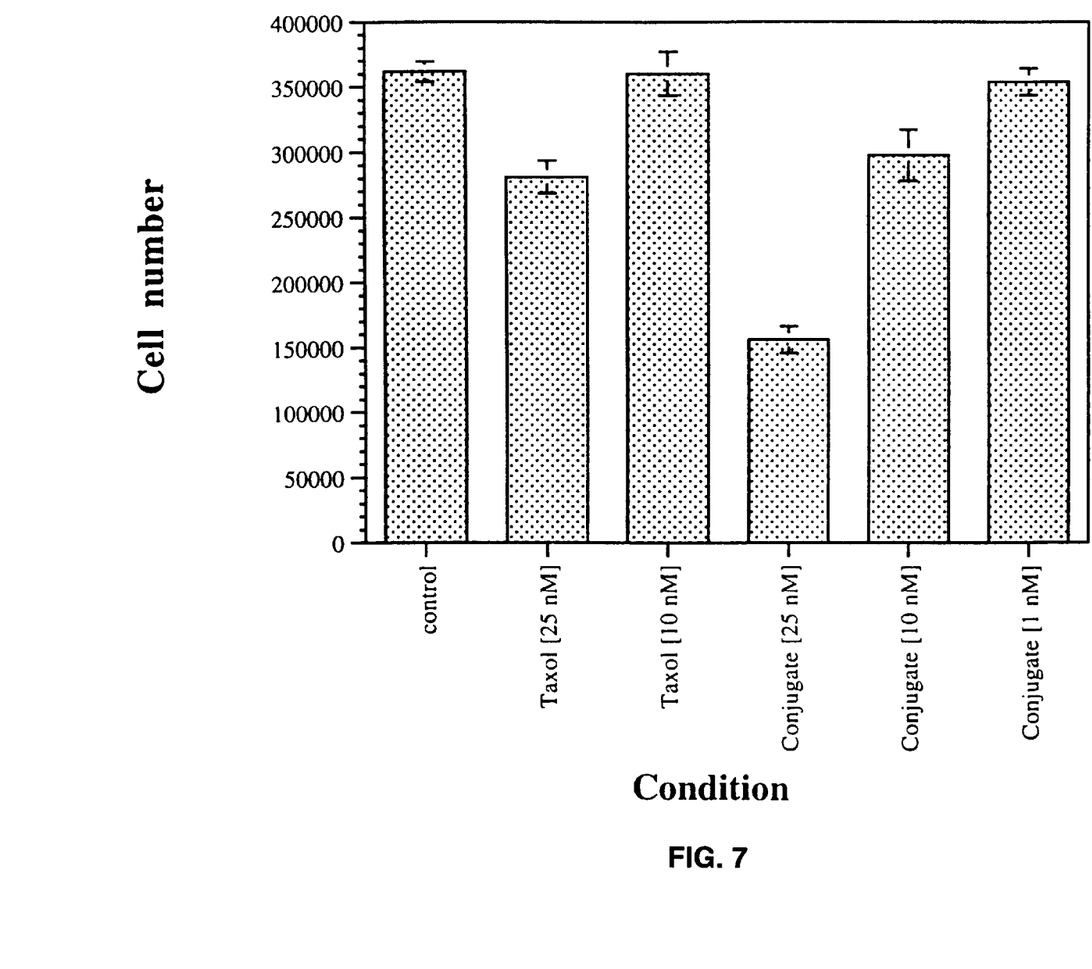
FIG. 7 shows cytotoxicity assays at day 4 post-treatment for the PIXPEGBBN [7–13] conjugate with underivatized paclitaxel as control. Cytotoxicity is evaluated at equimolar concentrations of the conjugate and paclitaxel molar ratio showing 3% (1 nM), 17% (10 nM), and 57% (25 nM) cell destruction by the conjugate as compared to that for the unconjugated paclitaxel with 0% and 20% at 10 nM and 25 nM, respectively.

To evaluate the cytotoxic activity of the conjugate relative to the intact, underivatized paclitaxel on the NCI-H1299 cells, 25 nM and 50 nM samples of paclitaxel and 10 nM and 30 nM solutions of the conjugate were incubated with the cells and the survival was assessed on day 4. This assay showed a significant improvement in cytotoxicity produced by the conjugate at both concentrations as compared to the free paclitaxel. While the free drug showed 23% (25 nM) and 51% (50 nM) of growth inhibition, he conjugate resulted in 53% and 70% inhibition at 25 nM and 50 nM, and respectively (FIG. 6). At equimolar concentrations, this assay showed 20% (25 nM) and 0% (10 nM) of cytotoxicity while those of the conjugate were 57%, 17% and 3%, at 25 nM, 10 nM, and 1 nM, respectively (FIG. 7). The fact that the peptide-conjugated paclitaxel shows improved cytotoxicities in a concentration-dependent manner, may be indicative of the specific, receptor-mediated delivery of the drug to the tumor cells.

Paclitaxel (Taxol) and docetaxel (Taxotere) are diterpenoid molecules with extremely high therapeutic potentials against breast, ovarian, and possibly other types of cancers with exceptional activities against refractory tumors. Although these compounds are currently in clinical use, a great deal of research is currently underway to improve their chemical, pharmacological and pharmaceutical properties. Major among these, are efforts to develop compounds with optimal aqueous solubility and lowered toxicities. Water-soluble paclitaxel derivatives with the ability to exert their antitumor activity with high selectivity will greatly enhance the therapeutic outcome of the treatment protocols applying this promising drug.

The present invention demonstrates the applicability of the prodrug approach to the design and synthesis of the first soluble tumor-recognizing paclitaxel derivative. The synthesis covalently grafted a BBN/GRP receptor ligand peptide to a heterobifunctional poly (ethylene glycol) chain followed by the ligation of the polyethylene glycol at the N-terminal, to the 2'-hydroxy group of paclitaxel, resulting in a molecule containing the three segments at a 1:1:1 molar ratio. The conjugate, designated PTXPEGBBN[7–13], was readily water soluble as well as being soluble in a number of organic solvents. The molecule showed retention of the BBN/GRP receptor-binding property of its peptide segment as well as the cytotoxicity of the paclitaxel moiety. Cytotoxicity assays, using human non-small cell lung cancer cell line NCI-H1299 and with underivatized paclitaxel as control, indicated significant improvement in cytotoxicity in a concentration-dependent manner.

The encouraging observations described in this report warrant further investigations on this and other congeners of the lead PTXPEGBBN[7–13] conjugate. Analogues with the paclitaxel moiety substituted at different sites and using different peptides, with affinities for different tumor cell surface receptors, have been designed and are currently in the synthetic pipeline in this laboratory. The synthesis of these novel molecules may start a new approach to the more efficient utilization of the taxane class of anticancer agents.

The following references were cited herein:
(1) Wani, et al., (1971) *J Am Chem Soc* 93, 2325–2327.
(2) Piccart, et al., (1995) *J Natl Cancer Inst* 87, 676–681.
(3) Holmes, et al., (1995) Taxane Anticancer Agents: Basic science and current status G. Georg, et al. (ed.) (eds.), pp 31–57, American Chemical Society, Washington, D.C.
(4) Arbuck, et al., (1995) Taxol Science and Applications M. Suffness (ed.)˜(eds.), pp 379–415, CRC, Boca Raton, Fla.
(5) Tishler, et al., (1992) *Cancer Res* 52, 3495–3497.
(6) O'Donnell, et al., (1998) *Cancer Biother Radiopharm* 13, 351–361.
(7) Distefano, et al., (1997) *Int J Cancer* 72, 844–850.
(8) Dorr, (1994) *Ann Pharmacother* 28, S11–S14.
(9) Sharma, et al., (1997) *Int J Cancer* 71, 103–107.
(10) Roland, et al., (1998) *Gynecol Oncol* 68, 178–182.
(11) Preston, (1996) *Eur J Cancer Care (Engl)* 5, 147–152.
(12) Hajek, et al., (1996) *Neoplasma* 43, 141–154.
(13) Postma, et al., (1995) *Ann Oncol* 6, 489–494.
(14) Maier-Lenz, et al., (1997) *Semin Oncol* 24, S19-16–S19-19.
(15) Goodwin, (1991) *Antib Immunoconj Radiopharm* 4, 427–434.
(16) Kohler, et al., (1975) *Nature* 256, 495–497.
(17) Unknown. (1998) *Science* 279, 323.
(18) Hoffman, et al., (1995) *J Labelled Comp Radiopharm* 37, 321–323.
(19) Greenwald, et al., (1995) *J Org Chem* 60, 331–336.
(20) Li, et al., (1996) *Anticancer Drugs* 7, 642–648.
(21) Safavy, A., unpublished data.
(22) Zalipsky, (1995) *Bioconjug Chem* 6, 150–165.
(23) Battey, et al., (1991) *Proc Natl Acad Sci USA* 88, 395–399.
(24) Safavy, et al., (1997) *Cancer* (Suppl) 80, 2354–2359.
(25) Ryan, et al., (1998) *J Biol Chem* 273, 13613–13624.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A pharmaceutical compound, wherein said compound comprising a taxane moiety conjugated to a receptor ligand peptide.

2. The pharmaceutical compound of claim 1, wherein said taxane moiety is a taxane derivative.

3. The pharmaceutical compound of claim 1, wherein said taxane is selected from the group consisting of paclitaxel (taxol) and taxotere (docetaxel).

4. The pharmaceutical compound of claim 1, wherein said taxane is paclitaxel or docetaxel, conjugated at a position selected from the group consisting of 2'-, 1-, 7- and 10-.

5. The pharmaceutical compound of claim 1, wherein said receptor ligand peptide is selected from the group consisting of a bombesin/gastrin-releasing peptide (BBN/GRP) receptor-recognizing peptide (BBN[7–13]), a somatostatin receptor recognizing peptide, an epidermal growth factor receptor recognizing peptide, a monoclonal antibody or a receptor recognizing carbohydrate.

6. The pharmaceutical compound of claim 1, wherein said compound is water soluble and tumor directed.

7. The pharmaceutical compound of claim 6, wherein said compound is readily soluble in water at the concentration of up to about 250 mg/mL.

8. The pharmaceutical compound of claim 6, wherein said tumor is selected from the group consisting of breast tumor, ovarian tumor, skin tumor, lung tumor, head tumor and neck tumor.

9. A method of synthesizing the pharmaceutical compound of claim 1, comprising the steps of:
   conjugating covalently said receptor ligand peptide to a solubilizing linker; and
   ligating the peptide-conjugated linkers to said taxane moiety.

10. The method of claim 9, wherein said solubilizing linker is ligated to said taxane moiety at the site selected from the group consisting of 2'-hydroxyl group, 2-hydroxyl group, 7-hydroxyl group and 10-hydroxyl group.

11. The method of claim 9, wherein the synthesized pharmaceutical compound has improved cytotoxicities in a concentration-dependent manner by a factor of 1.5–3 compared to corresponding unconjugated taxane moiety at an equimolar concentration.

12. A method of treating an individual having a cancer, comprising the step of:
   administering the pharmaceutical compound of claim 1 to said individual.

13. The method of claim 12, wherein said cancer is selected from the group consisting of breast cancer, ovarian cancer, skin carcinoma, lung carcinoma, head carcinoma and neck carcinoma.

14. The method of claim 12, wherein said pharmaceutical compound is administered by the means of injection or intravenous infusion.

* * * * *